US010624669B2

(12) United States Patent
Mangrum (10) Patent No.: US 10,624,669 B2
(45) Date of Patent: Apr. 21, 2020

(54) IMAGE-GUIDED DRAINAGE OF ABSCESSES

(71) Applicant: Wells Mangrum, Eau Claire, WI (US)

(72) Inventor: Wells Mangrum, Eau Claire, WI (US)

( * ) Notice: Subject to any disclaimer, the term of this patent is extended or adjusted under 35 U.S.C. 154(b) by 561 days.

(21) Appl. No.: 15/631,727

(22) Filed: Jun. 23, 2017

(65) Prior Publication Data

US 2018/0368882 A1  Dec. 27, 2018

(51) Int. Cl.
| | | |
|---|---|---|
| *A61B 17/34* | (2006.01) | |
| *A61B 5/00* | (2006.01) | |
| *A61M 5/32* | (2006.01) | |
| *A61M 27/00* | (2006.01) | |
| *A61B 34/00* | (2016.01) | |

(52) U.S. Cl.
CPC .......... *A61B 17/3403* (2013.01); *A61B 5/742* (2013.01); *A61B 17/3415* (2013.01); *A61B 17/3496* (2013.01); *A61B 34/00* (2016.02); *A61M 5/3287* (2013.01); *A61M 27/00* (2013.01); *A61B 2017/3405* (2013.01)

(58) Field of Classification Search
CPC ............ A61B 17/3403; A61B 17/3496; A61B 17/3423; A61B 17/3412; A61B 17/12109; A61B 17/320725; A61B 5/065; A61B 5/742; A61B 5/3287; A61B 34/00; A61B 34/20; A61B 1/0062; A61B 2017/3405; A61B 2017/3407; A61B 2017/3409; A61B 2017/3411; A61B 2017/3413; A61M 25/09041; A61M 27/00; A61N 1/0558; A61N 1/0502

See application file for complete search history.

(56) References Cited

U.S. PATENT DOCUMENTS

| | | | | |
|---|---|---|---|---|
| 5,232,440 | A | * | 8/1993 | Wilk .................... A61M 1/0062 604/543 |
| 2010/0268175 | A1 | * | 10/2010 | Lunsford ....... A61B 17/320725 604/272 |
| 2013/0178711 | A1 | * | 7/2013 | Avneri ............. A61B 17/12109 600/208 |
| 2014/0357986 | A1 | * | 12/2014 | Baldwin ................ A61B 5/065 600/424 |
| 2016/0317182 | A1 | * | 11/2016 | Mark .................. A61B 17/3496 |
| 2017/0095314 | A1 | * | 4/2017 | Baldwin ................ A61B 34/20 |
| 2017/0340891 | A1 | * | 11/2017 | Boggs .................. A61N 1/0558 |
| 2018/0126126 | A1 | * | 5/2018 | Ornelas Vargas .......................... A61M 25/09041 |
| 2019/0060642 | A1 | * | 2/2019 | Boggs, II ............. A61N 1/0502 |
| 2019/0125398 | A1 | * | 5/2019 | Baldwin ............ A61B 17/3423 |

* cited by examiner

*Primary Examiner* — Philip R Wiest (74) *Attorney, Agent, or Firm* — Brett A. Mangrum (57) ABSTRACT

In one embodiment, a system for image-guided drainage of abscesses includes a trocar configured to guide a tubular drain toward an abscess within the body of a patient. The trocar includes a joint portion pivotably coupling a proximal portion and a distal portion. The joint portion includes a locking mechanism that when engaged locks the proximal portion in place relative to the distal portion. The joint portion enables the trocar to pivot between an advancement position for advancing the trocar into the body of the patient and an image position for performing a radiology image of a partial advancement of the distal portion within the body of the patient. The image position reduces, relative to the advancement position, the angle between respective central axes of the proximal and distal portions.

20 Claims, 5 Drawing Sheets

IMAGE-GUIDED DRAINAGE OF ABSCESSES

TECHNICAL FIELD

The present disclosure relates generally to drainage of abscesses and in particular to methods and systems for image-guided drainage of abscesses.

BACKGROUND

Medical patients will on occasion develop deep abscesses that will not heal on their own unless surgically drained or drained percutaneously (through the skin). In general, the percutaneous drain is preferred if it is feasible. The percutaneous drain can be placed by palpation or by ultrasound if the abscess is superficial. However, if the abscess is deep, then other imaging technology, such as that provided by computed tomography (CT) imaging, may be used to guide placement of the drain. More specifically, CT images may be used, for example, to localize the abscess and allow the medical provider (e.g., a physician) to plan a route from skin surface to abscess that does not traverse important organs or blood vessels. Additionally, in particular instances, it may be desirable to use CT images not only to plan a route, but also to ensure proper placement of instruments during the procedure itself.

Prior attempts to use CT-guided drainage during a procedure were insufficient for a variety of reasons, and at times even led to tragic results and malpractice lawsuits. For example, certain instruments would not fit within a CT gantry unless they were significantly or even fully advanced into the patient, which often necessitated deep advancement with little or no CT guidance along the way. In the case of malposition, it was often difficult to reposition the catheter, which meant reinsertion was often necessary. Certain embodiments disclosed herein address these and other disadvantages.

BRIEF DESCRIPTION OF THE DRAWINGS

For a more complete understanding of the present disclosure and its features and advantages, reference is now made to the following description, taken in conjunction with the accompanying drawings, in which.

DESCRIPTION OF EXAMPLE EMBODIMENTS

Overview

In one embodiment, a system for image-guided drainage of abscesses includes a trocar configured to guide a tubular drain toward an abscess within the body of a patient. The trocar includes a joint portion pivotably coupling a proximal portion and a distal portion. The joint portion includes a locking mechanism that when engaged locks the proximal portion in place relative to the distal portion. The joint portion enables the trocar to pivot between an advancement position for advancing the trocar into the body of the patient and an image position for performing a radiology image of a partial advancement of the distal portion within the body of the patient. The image position reduces, relative to the advancement position, the angle between respective central axes of the proximal and distal portions.

In an alternative embodiment, a system for image-guided drainage of abscesses includes a trocar, a bipartite stiffening cannula, and a tubular drain. The trocar includes a retractable blade at a distal end thereof, which is configured to facilitate inserting the trocar into the body of a patient. The cannula includes a longitudinal passage configured to receive the trocar. The longitudinal passage includes a proximal portion and a distal portion, the proximal portion being more flexible than the distal portion. The tubular drain includes a longitudinal passage configured to receive both the trocar and the cannula. The tubular drain includes a proximal portion corresponding to the proximal portion of the cannula, and drainage holes proximate to a distal end thereof. The trocar is configured to engage the cannula and the drain, such that advancement of the trocar into the body of the patient advances the cannula and the drain into the body. The respective proximal portions of the cannula and the drain are sufficiently flexible for each to achieve a bent state in response to withdrawal of the trocar from the cannula and the drain, such that the bent state reduces the length of the cannula disposed along a central axis of the distal portion of the cannula.

In a method embodiment, a method for image-guided drainage of abscesses within a body of a patient includes inserting less than half the total length of a drain into the body of the patient along an axis of insertion. The drain is bent by changing the angle of a proximal portion of the drain outside of the body of the patient relative to a distil portion of the drain inside the body of the patient, such that the maximum distance of the drain along the axis of its insertion into the body of the patient is reduced. While the drain is in a bent state, a medical image of the drain within the body of the patient is generated using radiant energy. The drain is realigned along the axis of its insertion into the body. The drain is advanced further into the body toward an abscess, based on the medical image of the drain.

Technical advantages of various embodiments of the present disclosure include the ability to obtain certain images of instruments even if only partially advanced within a body. For example, using certain embodiments disclosed herein, a physician can acquire one or more intermediate stage computed tomography (CT) images to verify the accurateness of the depth and angle of partially-advanced instruments. Certain embodiments may decrease the risk of injury to adjacent structures and may also decrease the need for multiple punctures. Particular embodiments may obviate the need for time-consuming and complicated procedures, such as, for example, those associated wire manipulations of the Seldinger technique. Embodiments will also obviate the need for the Tandem-Trocar technique. In this technique, the trocar with mounted drain is advanced in one step from skin surface to abscess following the course of the tandem needle; no intermediate CT images are acquired in the Tandem-Trocar technique because the partially advanced trocar will often not fit in the CT gantry. Other technical advantages of the present disclosure will be readily apparent to one skilled in the art from the teachings of the present disclosure. Moreover, while specific advantages have been enumerated above, various embodiments may include all, some, or none of the enumerated advantages.

DESCRIPTION OF EXAMPLE EMBODIMENTS

Various embodiments are now described with reference to the drawings, wherein like reference numerals are used to refer to like elements throughout. In the following description, for purposes of explanation, numerous specific details are set forth in order to provide a thorough understanding of one or more embodiments. However, this disclosure may be practiced without some or all of these specific details, as will be evident to one having ordinary skill in the art. In other instances, well-known process steps or structures have not been described in detail in order not to unnecessarily obscure this disclosure. In addition, while the disclosure is described in conjunction with the particular embodiments, it should be understood that this description is not intended to limit the disclosure to the described embodiments. To the contrary, the description is intended to cover alternatives, modifications, and equivalents as may be included within the spirit and scope of the disclosure as defined by the appended claims.

Medical patients will on occasion develop deep abscesses that will not heal on their own unless surgically drained or drained percutaneously (through the skin). In general, the percutaneous drain is preferred if it is feasible. The percutaneous drain can be placed by palpation or by ultrasound if the abscess is superficial. However, if the abscess is deep, then other imaging technology, such as that provided by CT imaging, may be used to guide placement of the drain. More specifically, CT images may be used, for example, to localize the abscess and allow the medical provider (e.g., a physician) to plan a route from skin surface to abscess that does not traverse important organs or blood vessels. Additionally, in particular instances, it may be desirable to use CT images not only to plan a route, but also to ensure proper placement of instruments during the procedure itself.

Prior attempts to use CT-guided drainage during a procedure were insufficient for a variety of reasons, and at times even led to tragic results and malpractice lawsuits. For example, certain instruments would not fit within a CT gantry unless they were significantly or even fully advanced into the patient, which often necessitated deep advancement with little or no CT guidance along the way. In the case of malposition, it was often difficult to reposition the catheter, which meant reinsertion was often necessary. Certain embodiments disclosed herein address these and other disadvantages.

Technical advantages of various embodiments of the present disclosure include the ability to obtain certain images of instruments even if only partially advanced within a body. For example, using certain embodiments disclosed herein, health care providers can acquire one or more intermediate stage CT images to verify the accurateness of the depth and angle of partially advanced instruments. Certain embodiments may decrease the risk of injury to adjacent structures and may also decrease the need for multiple punctures. Particular embodiments may obviate the need for time-consuming and complicated procedures, such as, for example, those associated wire manipulations (e.g., using the Seldinger technique). Embodiments will also obviate the need for the Tandem-Trocar technique. In this technique, the trocar with mounted drain is advanced in one step from skin surface to abscess following the course of the tandem needle; no intermediate CT images are acquired in the Tandem-Trocar technique because the partially advanced trocar will often not fit in the CT gantry. Other technical advantages of the present disclosure will be readily apparent to one skilled in the art from the teachings of the present disclosure. Moreover, while specific advantages have been enumerated above, various embodiments may include all, some, or none of the enumerated advantages.

Figure 1:
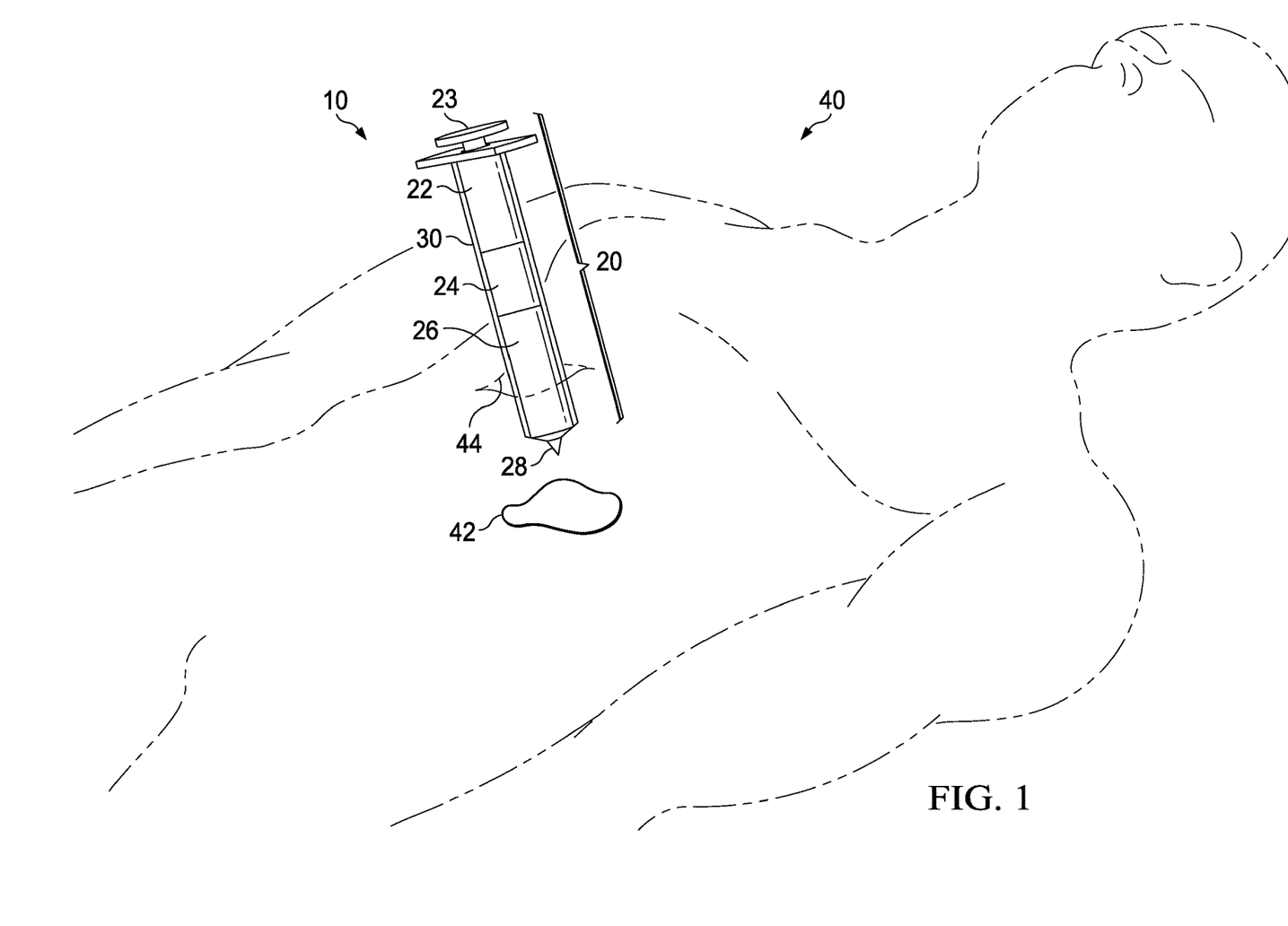
FIG. 1 is a simplified perspective view illustrating a system that may facilitate an image-guided abscess drain, according to an example embodiment.

FIG. 1 is a simplified perspective view illustrating a system 10 that may facilitate an image-guided abscess drain, according to an example embodiment. In the illustrated embodiment, system 10 generally includes a lockable and bendable trocar 20 configured to engage and guide a drainage catheter 30. For ease of reference, the trocar 20 is symbolically divided into three main sections: a proximal portion 22, a joint portion 24, and a distal portion 26. The proximal portion 22 may include a handle 23 at an end thereof, which among other things may facilitate manipulating system 10. As explained further below, the joint portion 24 generally enables the proximal portion 22 to pivot or bend relative to the distal portion 26 (or vice versa). In certain embodiments, the joint portion 24 includes a locking mechanism that when engaged locks the proximal and distal portions 22 and 26 relative to each other, at a desired angle (e.g., an angle within the range of 0 degrees to 270 degrees; however, the locking mechanism may be designed to lock in any desired angle). The distal portion 26 may include a blade 28 that facilitates advancing the trocar 20 through a patient 40 and toward an abscess 42 to be drained. In certain embodiments, blade 28 may be retractable.

Drainage catheter 30 is generally a hollow tube that may be used for insertion into a body to allow drainage of fluids, such as that found in an abscess 42. In the illustrated embodiment, drainage catheter 30 is configured to fit around trocar 20 and to be guided to a location within an abscess 42 by trocar 20. Once guided within the abscess 42, drainage catheter 30 may be manipulated to coil within the abscess 42. Fluid, such as pus, may then enter holes located at the coiled tip of drainage catheter 30; and the fluid may then travel through the hollow tube of the drainage catheter 30 out of the body of patient 40. In various embodiments, drainage catheter 30 is made of sufficiently flexible material to enable it to pivot and bend in response to manipulation of joint portion 24 of trocar 20. Additionally, or alternatively, drainage catheter 30 may itself include a joint portion substantially similar in structure and function to joint portion 24 of trocar 20, such that both joint portions may be cooperatively manipulated together to effect pivoting of system 10 as desired.

In operation, as shown in FIG. 1, a procedure to drain a particular abscess 42 may include partially advancing system 10 past the abdominal wall 44 of patient 40 and toward an abscess 42. Joint portion 24 of trocar 20 may initially be in a locked state, which in certain instances may facilitate an accurate advancement angle for system 10. As shown in FIG. 1, for example, joint portion 24 may be locked in a position that aligns the proximal portion 22 and distal portion 26 along the same or substantially the same central longitude axis A of trocar 20. However, joint portion 24 may be configured to lock in any desired angle of the proximal portion 22 relative to the distal portion 26.

In certain instances, it may be desirable to use some form of imaging (e.g., a CT scan) to confirm the accurateness of the depth and angle of a partially advanced trocar 20 before advancing it any further. However, the dimensions of system 10 may be such that if the trocar 20 is in a position that maximizes its length along a single axis (e.g., in the locked position along axis A shown in FIG. 1), then system 10 may not fit within the imaging device. In certain embodiments, joint portion 24 may be configured to transition the trocar 20 between multiple positions including, for example, at least an elongated position that may be preferable for advancement (e.g., the example position shown in FIG. 1), and a bent or deformed position that may be preferable for certain imaging processes (e.g., the example position shown in FIG. 2).

Figure 2:
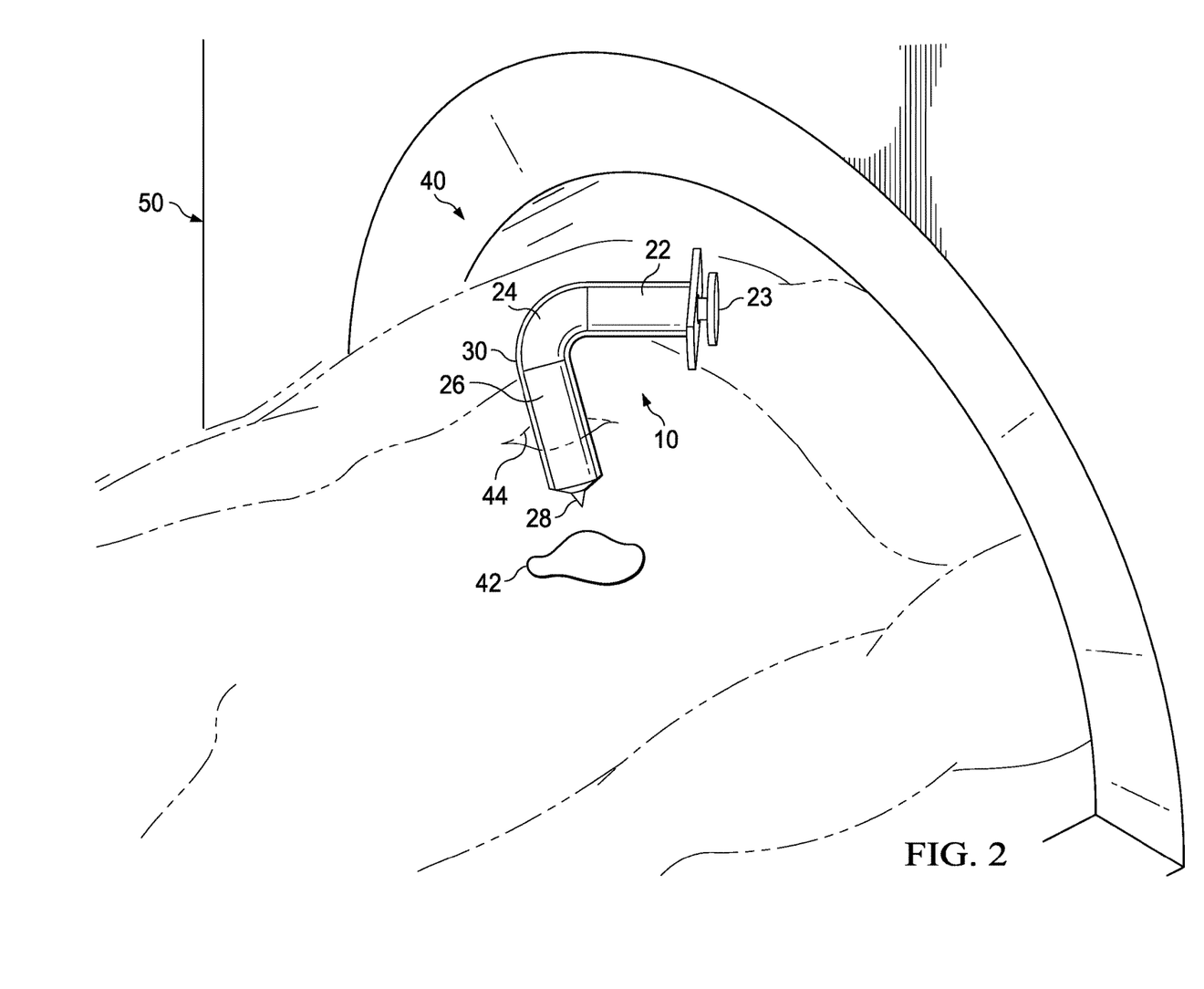
FIG. 2 is a simplified perspective view illustrating the system of FIG. 1 in a bent or deformed state that may facilitate imaging system while it is partially or fully advanced within a patient.

FIG. 2 is a simplified perspective view illustrating the system 10 of FIG. 1 in a bent or deformed state that may facilitate imaging system 10 while it is partially or fully advanced within a patient 40. To achieve the bent or deformed state while system 10 is advanced, joint portion 24 may be used to pivot the proximal portion 22 of trocar 20 relative to the distal portion 26. If joint portion 24 has a locking mechanism, then joint portion 24 may include a mechanism that needs to be actuated to transition joint portion 24 from a locked state into an unlocked or released state that enables pivoting. For example, joint portion 24 may have a mechanical release that is actuated by pressing a button or by otherwise applying pressure to move a locking member; however, any suitable release mechanism may be used.

In certain embodiments, the pivot action of joint portion 24 may be sufficiently loose to allow the proximal portion 22 to pivot naturally under the force of gravity. Alternatively, the pivot action of joint portion 24 may be sufficiently stiff to require manual manipulation to achieve a desired pivot angle. If controlling the pivot angle is desirable, joint portion 24 may include any of a variety of mechanisms that may facilitate controlling the pivot angle of system 10, such that system 10 does not interfere with either the imaging device or the body of patient 40 during an imaging process. As shown in FIG. 2, for example, joint portion 24 has a "C-shaped" hinge configured to control a minimum acute angle to which joint portion 24 may pivot; however, any suitable configuration may be used for joint portion 24. In particular embodiments, joint 24 may comprise multiple lockable hinges, each providing an independent pivot point relative to the other hinges (e.g., each hinge disposed slightly apart from each other along the longitudinal length of trocar 22); and such a group of lockable hinges may collectively and cooperatively be capable of pivoting trocar 22 to any of a number of possible configurations.

While certain embodiments disclosed herein may make use of a particular lockable and bendable trocar 22, various alternative embodiments may use alternative trocars, or no trocar at all. Certain alternative embodiments are described, by way of example, with reference to FIGS. 3 and 4.

Figure 3:
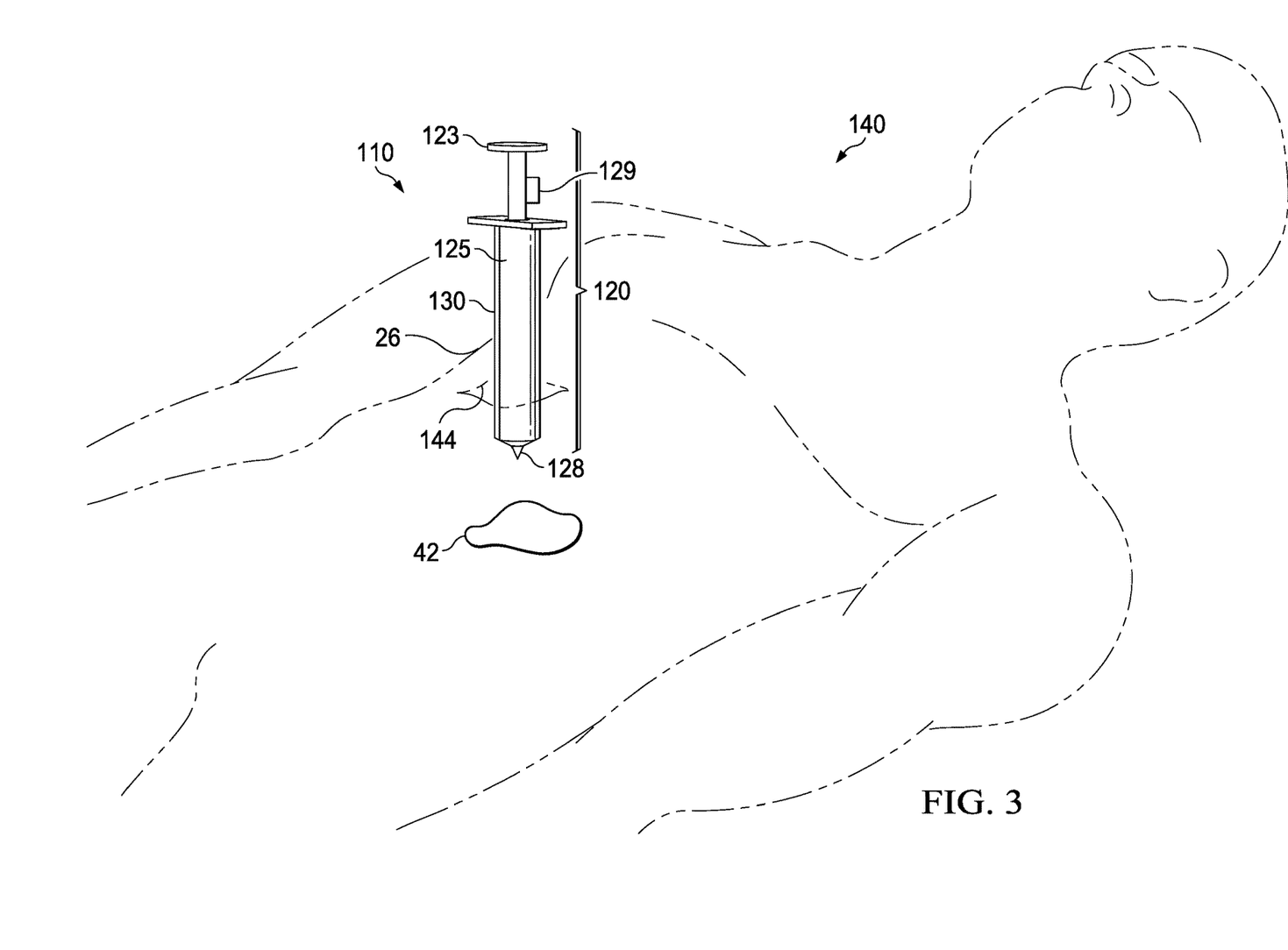
FIG. 3 is a simplified perspective view illustrating a system that may facilitate an image-guided abscess drain, according to an alternative example embodiment.

FIG. 3 is a simplified perspective view illustrating a system 110 that may facilitate an image-guided abscess drain, according to an alternative example embodiment. In the illustrated embodiment, system 110 generally includes retractable trocar 120 configured to engage and guide a cannula 125, which itself is configured to engage a drainage catheter 130.

In certain embodiments, trocar 120 may be substantially similar in structure and function to trocar 20 of FIGS. 1 and 2. In the illustrated embodiment, trocar 120 includes a handle 23 at a proximal end thereof, which among other things may facilitate manipulating system 110. Trocar 120 also includes a blade 128 at a distal end thereof, which among other things may facilitate advancing the trocar 120 through a patient 140 and toward an abscess 142 to be drained. Blade 128 may be retractable (e.g., by manipulating a lever 129), which among other things may facilitate inserting and withdrawing trocar 120 from system 110 without damaging either cannula 125 or drainage catheter 130.

Cannula 125 is generally a bipartite stiffening cannula that has a hollow, longitudinal passage configured to receive and be engaged by trocar 120. Additionally, as shown in FIG. 3, cannula 125 may have a bushing that engages drainage catheter 130, such that the entire system 110 advances into the patient's body 140 in response to advancement of trocar 120.

Drainage catheter 130 is generally a hollow tube that may be used for insertion into a body to allow drainage of fluids, such as that found in an abscess 142. In certain embodiments, drainage catheter 130 is substantially similar in structure and function to drainage catheter 30 described above with reference to FIGS. 1 and 2. In the illustrated embodiment, drainage catheter 130 drainage catheter 30 is configured to fit around and be engaged by cannula 125. Once guided within the abscess 142, drainage catheter 130 may be manipulated to coil within the abscess 142. Fluid, such as pus, may then enter holes located at the coiled tip of drainage catheter 130; and the fluid may then travel through the hollow tube of the drainage catheter 130 out of the body of patient 140.

In operation, as shown in FIG. 3, a procedure to drain a particular abscess 142 may include partially advancing system 110 past the abdominal wall 144 of patient 140 and toward an abscess 142. In certain instances, it may be desirable to use some form of imaging (e.g., a CT scan) to confirm the accurateness of the depth and angle of a partially advanced trocar 120 before advancing it any further. However, the dimensions of system 110 may be such that the entire system (including trocar 120) may not fit within the imaging device (e.g., a gantry thereof). In certain embodiments, trocar 123 may be temporarily withdrawn from system 110, which may enable both enable cannula 125 and drainage catheter 130 to achieve a bent or deformed state that may be preferable for certain imaging processes (e.g., the example state shown in FIG. 4).

Figure 4:
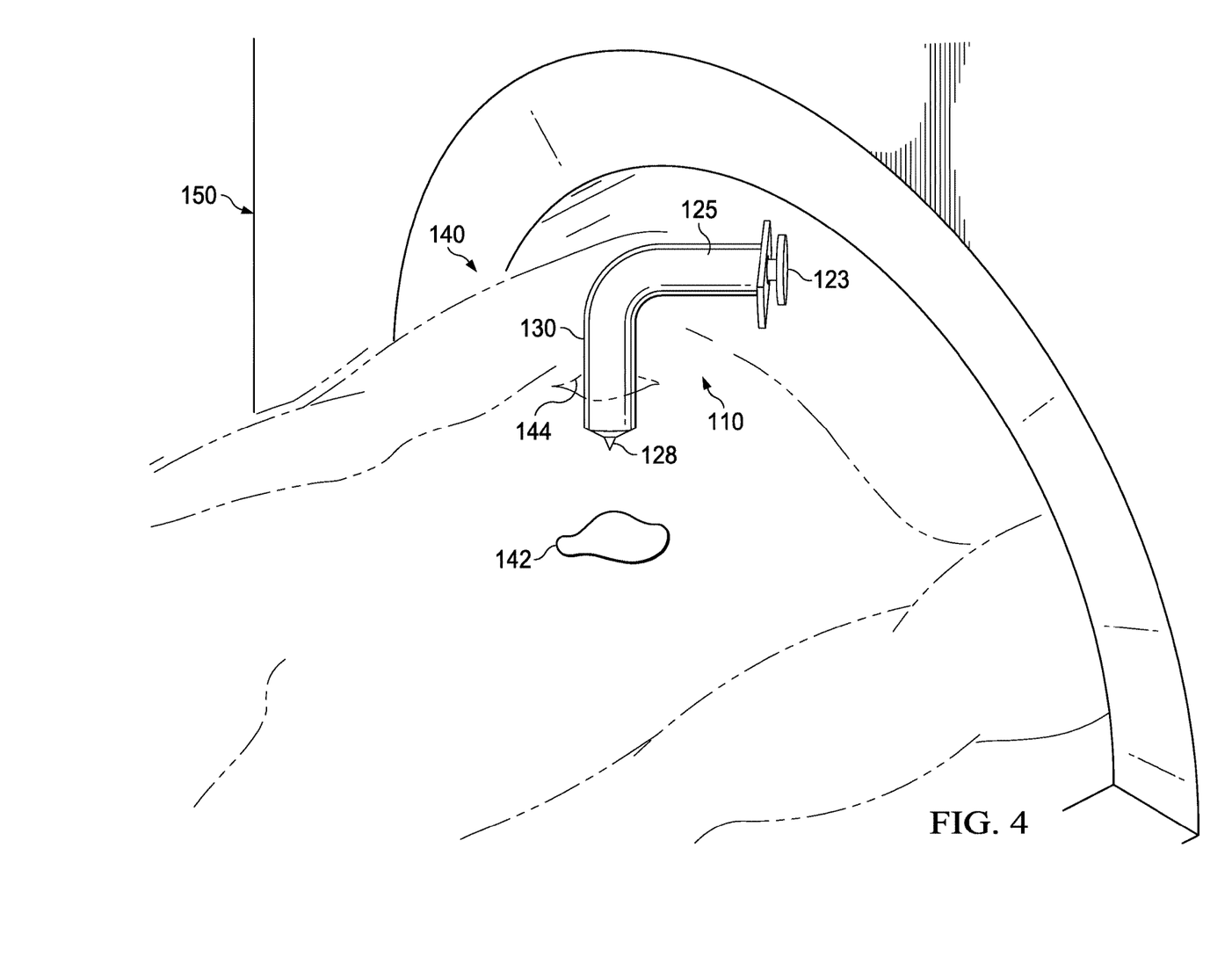
FIG. 4 is a simplified perspective view illustrating the system of FIG. 3 in a bent or deformed state that may facilitate imaging system while it is partially or fully advanced within a patient.

FIG. 4 is a simplified perspective view illustrating the system 110 of FIG. 3 with the trocar 120 withdrawn, which enables cannula 125 and drainage catheter 130 to achieve a bent or deformed state. Such a state may sufficiently reduce the length of the cannula disposed along the central axis of the distal portion of the cannula 125 to enable the cannula 125 and drainage catheter 130 to fit within a gantry of a radiology-imaging device (e.g., an X-ray device capable of performing CT imaging). In certain embodiments, the respective proximal portions of the cannula 125 and the drainage catheter 130 are sufficiently flexible for each to bend under gravity if the trocar 120 is withdrawn from the cannula 125 and the drainage catheter 130. In various embodiments, the bent or deformed state may be achievable, for example, even if less than half of total length of the drainage catheter 130 is advanced into the body of the patient.

After one or more images are generated, trocar 120 may be reinserted and may newly engage the cannula 125 and the drainage catheter 130, such that advancement of the trocar 120 further into the body of the patient causes further advancement of both the cannula and the drain into the body of the patient. The blade 128 of trocar 120 may be retracted while it is being reinserted, so as to avoid damaging either the cannula 125 or the drainage catheter 130. Upon fully reinserting trocar 120, the blade 128 of trocar may then be extended to facilitate advancing system 110 further toward the abscess to be drained.

Figure 5:
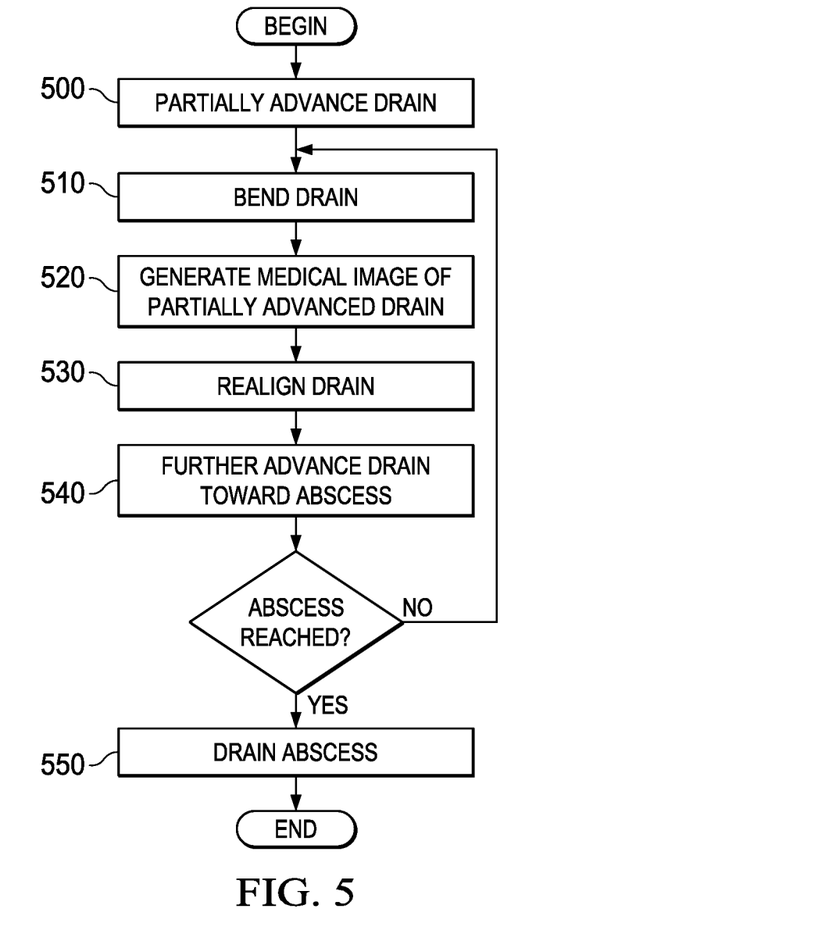
FIG. 5 illustrates a method for image-guided drainage of abscesses within a body of a patient.

FIG. 5 illustrates a method for performing image-guided drainage of an abscess according to certain embodiments. In step 500, a distal portion of a drain (e.g., drainage catheter 30 or 130) is inserted into the body of the patient and advanced toward an abscess. In certain embodiments, a percutaneous drain may be preferred if it is feasible. Other components may be used to assist in advancing the drain toward the abscess. For example, as disclosed with references to FIGS. 1 through 4, a trocar (e.g., trocars 20 or 120) or a cannula (e.g., cannulas 25 or 125) may be configured to engage the drain, such that advancement of the engaging component guides the advancement of the drain toward the abscess.

In certain instances, it may be desirable to acquire one or more intermediate stage CT images to verify the accurateness of the depth and angle of the partially-advanced drain. For example, it may be desirable to image the depth and angle of the drain when less than half the total length of a drain is advanced into the body of the patient along an axis of insertion. However, the partially-advanced drain may not fit within the gantry of the imaging device if it is fully extended along the axis of insertion.

In step 510, the drain is bent or otherwise deformed by changing the angle of a proximal portion of the drain outside of the body of the patient relative to a distil portion of the drain inside the body of the patient, such that the maximum distance of the drain along the axis of its insertion into the body of the patient is reduced.

In step 520, while the drain is bent or otherwise deformed, a medical image of the drain within the body of the patient is generated. For example, a medical image may be generated using CT-imaging; however, any suitable imaging technique(s) may be used. In step 530, the drain is realigned along the axis of its insertion into the body. In step 540, the drain is advanced further into the body toward the abscess (e.g., by advancing a trocar or cannula that engages the drain), based on the medical image of the drain.

In certain embodiments, one or more of steps 510, 520, and 530 may be repeated as needed to guide the advancement of the drain directly into the abscess. For example, a determination may be made after an image-guided advancement of the drain as to whether the drain has successfully accessed the abscess. In certain instances, the determination may be based at least in part on whether a calculated distance of advancement has been achieved, wherein the distance of advancement is calculated at least in part using an image of a prior drain position within the body of the patient. Additionally, or alternatively, the determination may be made based at least in part on a newly generated image of the present location of the drain within the body of the patient, using the techniques described herein.

In step 550, the abscess is drained. In certain embodiments, once the drain is successfully guided within the abscess, the engaging components (e.g., a trocar or cannula, or both), if any, may be withdrawn; and the drain may be manipulated to coil within the abscess. Fluid, such as pus, may then enter holes located at the coiled tip of drain; and the fluid may then travel through the hollow tube of the drain out of the body of patient.

The components of the systems and apparatuses disclosed herein may be integrated or separated. For example, in certain embodiments, the trocar 20 and drainage catheter 30 of FIG. 1 may be integrally constructed as one device having an integrated joint 24 at or proximate to midshaft. Moreover, the operations of the systems and apparatuses may be performed by more, fewer, or other components. The methods may include more, fewer, or other steps. Additionally, steps may be performed in any suitable order. Particular operations of the systems and apparatuses disclosed herein may be performed using any suitable logic embodied in computer-readable media. As used in this document, "each" refers to each member of a set or each member of a subset of a set.

To aid the Patent Office, and any readers of any patent issued on this application, in interpreting the claims appended hereto, applicant notes that there is no intention that any of the appended claims invoke paragraph 6 of 35 U.S.C. § 112 as it exists on the date of filing hereof unless the words "means for" or "step for" are explicitly used in the particular claim.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

What is claimed is:

1. A system for image-guided drainage of abscesses comprising:
a trocar configured to guide a tubular drain toward an abscess within the body of a patient, the trocar comprising a joint portion pivotably coupling a proximal portion and a distal portion, the joint portion comprising a locking mechanism that when engaged locks the proximal portion in place relative to the distal portion, the joint portion enabling the trocar to pivot between an advancement position for advancing the trocar into the body of the patient and an image position for performing a radiology image of a partial advancement of the distal portion within the body of the patient, the image position reducing, relative to the advancement position, the angle between respective central axes of the proximal and distal portions.

2. The system of claim 1, further comprising the tubular drain, the tubular drain comprising:
a longitudinal passage configured to receive the trocar; and
drainage holes proximate to a distal end of the tubular drain.

3. The system of claim 1, further comprising the tubular drain and a cannula disposed between the trocar and the tubular drain, the tubular drain comprising:
a longitudinal passage configured to receive the trocar; and drainage holes proximate to a distal end of the tubular drain.

4. The system of claim 1, wherein the image position reduces, relative to the advancement position, the length of the trocar extending along an axis of insertion.

5. The system of claim 1, wherein the locking mechanism, when engaged, locks the proximal and distal portions in an aligned configuration, such that the angle between respective central axis of the proximal and distal portions is zero.

6. The system of claim 1, the trocar further comprising a retractable blade configured to toggle between an exposed position and an unexposed position.

7. The system of claim 1, the joint portion further comprising a C-hinge.

8. The system of claim 1, the joint portion further comprising a plurality of hinges.

9. The system of claim 1, wherein the radiology image is a computed tomography (CT) image.

10. A system for image-guided drainage of abscesses comprising:
- a trocar comprising a retractable blade at a distal end thereof, the blade configured to facilitate inserting the trocar into the body of a patient;
- a bipartite stiffening cannula comprising a longitudinal passage configured to receive the trocar, the longitudinal passage comprising a proximal portion and a distal portion, the proximal portion being more flexible than the distal portion; and
- a tubular drain comprising a longitudinal passage configured to receive both the trocar and the cannula, the tubular drain comprising:
  - a proximal portion corresponding to the proximal portion of the cannula, and drainage holes proximate to a distal end thereof;
- wherein the trocar is configured to engage the cannula and the drain, such that advancement of the trocar into the body of the patient advances the cannula and the drain into the body; and
- wherein the respective proximal portions of the cannula and the drain are sufficiently flexible for each to achieve a bent state in response to withdrawal of the trocar from the cannula and the drain, such that the bent state reduces the length of the cannula disposed along a central axis of the distal portion of the cannula.

11. The system of claim 10, wherein the respective proximal portions of the cannula and the drain are sufficiently flexible for each to bend under gravity if the trocar is withdrawn from the cannula and the drain.

12. The system of claim 10, wherein the bent state is achievable with less than half of the total length of the cannula advanced into the body of a patient and, once achieved, sufficiently reduces the length of the cannula disposed along the central axis of the distal portion of the cannula to enable the cannula and drain to fit within a gantry of an X-ray device capable of computed tomography (CT) imaging.

13. The system of claim 10, wherein, in the event the trocar is withdrawn from both the cannula and the drain, the cannula and the drain are further configured to be newly engaged by the trocar upon reinsertion of the trocar within the cannula and the drain, such that advancement of the trocar further into the body of the patient causes further advancement of both the cannula and the drain into the body of the patient.

14. The system of claim 10, wherein the proximal portion of the cannula comprises one or more hinges.

15. The system of claim 10, wherein a distal portion of the tubular drain is at least as flexible as the proximal portion corresponding to the flexible portion of the cannula.

16. The apparatus of claim 10, the trocar further comprising a lever at a proximal end of the trocar, the lever configured to advance and retract the retractable blade.

17. A method for image-guided drainage of abscesses within a body of a patient, comprising:
- inserting less than half the total length of a drain into the body of the patient along an axis of insertion;
- bending the drain by changing the angle of a proximal portion of the drain outside of the body of the patient relative to a distil portion of the drain inside the body of the patient, such that the maximum distance of the drain along the axis of its insertion into the body of the patient is reduced;
- while the drain is in a bent state, generating a medical image of the drain within the body of the patient using radiant energy;
- realigning the entire length of the drain along the axis of its insertion into the body; and
- advancing the drain further into the body toward an abscess, based on the medical image of the drain.

18. The method of claim 17, wherein advancing the drain further into the body further comprises engaging the drain with a trocar.

19. The method of claim 17, wherein advancing the drain further into the body further comprises engaging the drain with a cannula.

20. The method of claim 17, wherein generating the medical image of the drain within the body of the patient comprises generating a computed tomography (CT) image.

* * * * *